United States Patent
Qi et al.

(10) Patent No.: US 8,148,587 B2
(45) Date of Patent: Apr. 3, 2012

(54) METHOD FOR PRODUCING LIGHT OLEFINS FROM METHANOL OR/AND DIMETHYL ETHER

(75) Inventors: Yue Qi, Dalian (CN); Zhongmin Liu, Dalian (CN); Zhihui Lv, Dalian (CN); Hua Wang, Dalian (CN); Changqing He, Dalian (CN); Lei Xu, Dalian (CN); Jinling Zhang, Dalian (CN); Xiangao Wang, Dalian (CN)

(73) Assignee: Dalian Institute of Chemical Physics, Chinese Academy of Sciences, Dalian (CN)

( * ) Notice: Subject to any disclaimer, the term of this patent is extended or adjusted under 35 U.S.C. 154(b) by 331 days.

(21) Appl. No.: 12/529,912

(22) PCT Filed: Jul. 27, 2007

(86) PCT No.: PCT/CN2007/002267
§ 371 (c)(1),
(2), (4) Date: Sep. 3, 2009

(87) PCT Pub. No.: WO2008/106841
PCT Pub. Date: Sep. 12, 2008

(65) Prior Publication Data
US 2010/0063336 A1    Mar. 11, 2010

(30) Foreign Application Priority Data
Mar. 7, 2007   (CN) .......................... 2007 1 0064232

(51) Int. Cl.
   *C07C 1/20*   (2006.01)

(52) U.S. Cl. ........ 585/314; 585/315; 585/324; 585/408; 585/469; 585/638; 585/639; 585/640; 585/733; 422/200

(58) Field of Classification Search ................. 585/314, 585/315, 324, 408, 469, 638, 639, 640, 733; 422/200
See application file for complete search history.

(56) References Cited

U.S. PATENT DOCUMENTS
6,399,844 B1 *  6/2002  van Dijk ....................... 585/639

FOREIGN PATENT DOCUMENTS
| CN | 1404463 A | 3/2003 |
| CN | 1685034 A | 10/2005 |
| EP | 1 508 555 A1 * | 2/2005 |

OTHER PUBLICATIONS

Non-Final Office Action, issued by Korean Intellectual Property Office on May 9, 2011.

* cited by examiner

*Primary Examiner* — Prem C Singh
(74) *Attorney, Agent, or Firm* — Knobbe, Martens, Olson & Bear, LLP

(57) ABSTRACT

The present invention provides a method for producing Lower olefin from the feed of methanol or/and dimethyl ether, characterized in that methanol or/and dimethyl ether are divided proportionally to be fed at 3 reaction zones; and the desired distribution of the olefin product is obtained by modulating the feeding ratio among the 3 reaction zones and the reaction conditions in each reaction zone.

12 Claims, 1 Drawing Sheet

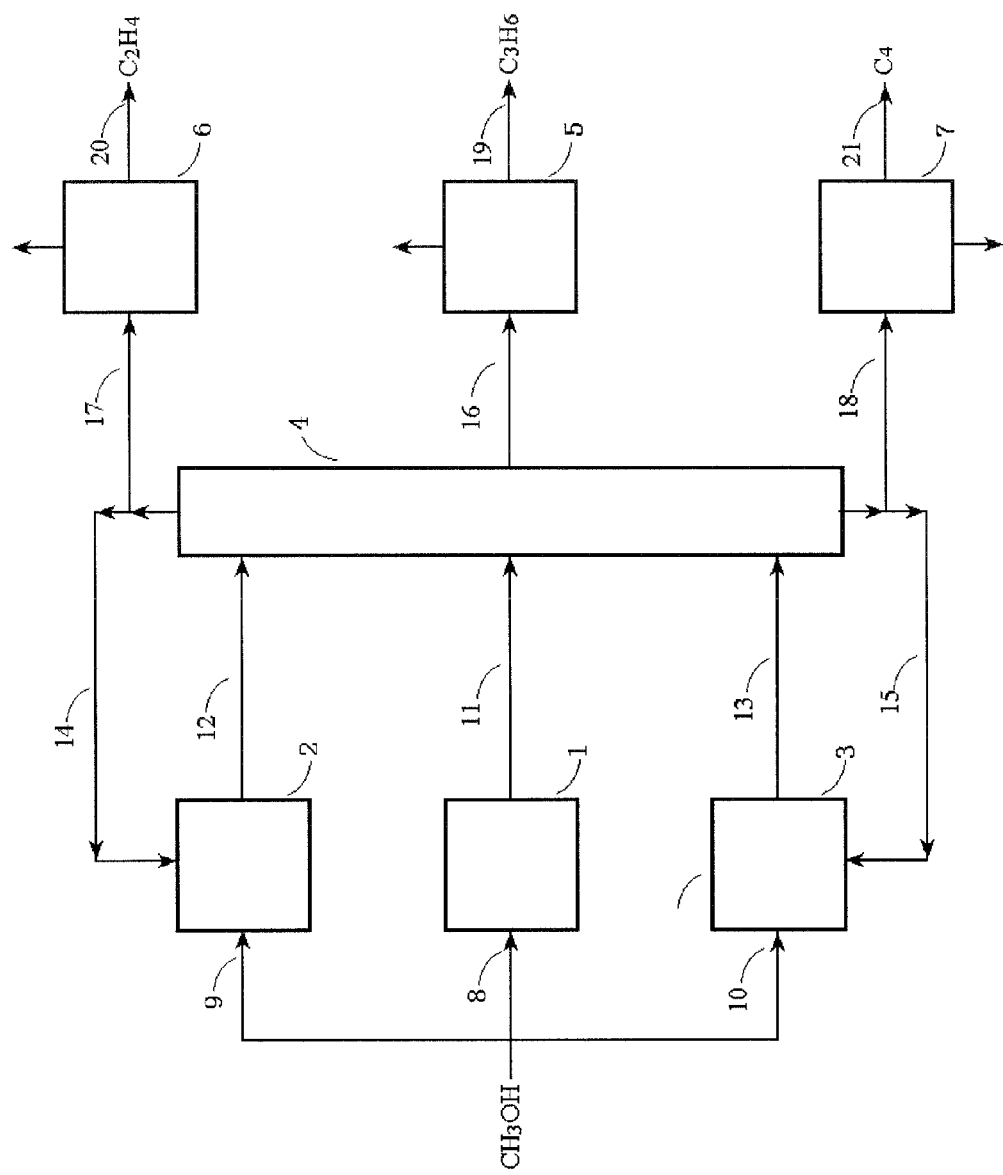

METHOD FOR PRODUCING LIGHT OLEFINS FROM METHANOL OR/AND DIMETHYL ETHER

This application is U.S. National Phase of International Application PCT/CN2007/002267, filed Jul. 27, 2007 designating the U.S., and published in Chinese as WO 2008/106841 on Sep. 12, 2008.

FIELD OF THE INVENTION

The present invention relates to a method for converting methanol or/and dimethyl ether into light olefins.

BACKGROUND OF THE INVENTION

Light olefins such as ethylene, propylene, etc. are the basic raw material for chemical industry. Conventionally, ethylene and propylene mainly come from steam cracking of hydrocarbon feedstock such as naphtha, light diesel oil, hydrogenation cracking tail oil and the like. Recently, as the price of crude oil has been dramatically rising up, the cost for producing ethylene and propylene from the above feedstock has been increasing. Also, in the conventional processes for producing ethylene and propylene, high temperature tubular furnace cracking technologies with a high energy consumption are generally used. All these factors urge the development of new olefin production technologies. Novel technical pathways of preparation of lower olefins from non-petroleum materials have caught much attention in the past years. Among those, the one, characterized in that coal or natural gas is transformed into methanol through syngas, and then methanol is transformed into lower olefins, has been of extensive interest. The process of selectively producing light olefins from methanol (or dimethyl ether generated from the dehydration of methanol) in the presence of molecular sieve catalysts is referred to as MTO process. The methods and technologies for transforming methanol into light olefins are closely correlated to the catalysts used therein. It is well known that two classes of catalysts are used in these processes. One class is the catalysts based on ZSM-5 molecular sieves with medium size micropores, characterized by higher yield of propylene and lower yield of ethylene in the distribution of the products, slightly lower total yield of ethylene and propylene, strong anti-coking ability of the catalysts and longer operating cycle. The reaction techniques suitable for the above class are usually fixed bed reaction techniques with periodical switches between reactions and regenerations. Another class of catalysts is based on the molecular sieves with smaller pore size, characterized by high total yield of ethylene and propylene as well as higher yield of ethylene in the product. Because this class of catalysts has a higher coking rate, the processes generally utilize fluidized bed techniques with continuous reaction-regeneration of the catalysts.

U.S. Pat. No. 6,613,951 B1 and Chinese patent CN1352627A disclose methods for converting methanol or/and dimethyl ether into C2-C4 olefins, wherein the feed are contacted with a catalyst containing a 10-ring zeolite under 370-480° C. with a methanol partial pressure of 30-150 psia.

Chinese patent CN1302283A discloses a method for converting methanol or/and dimethyl ether into C2-C4 olefins and aromatics higher than C9, wherein a portion of the aromatics is returned back to the reactor and co-fed with methanol or dimethyl ether under 350-480° C. to increase the yield of olefins. U.S. Pat. No. 6,506,954 B1 discloses a method for converting methanol or/and dimethyl ether into C2-C4 olefins, wherein aromatic compounds are added to increase the yield of olefin. The catalysts used in the method are porous crystalline materials with a pore size larger than the dynamic diameter of aromatic compounds. Reactions are conducted at 350-480° C. The partial pressure for methanol is not lower than 10 psia. The 2,2-dimethyl butane diffusion coefficient of the catalysts is 0.1-20 sec$^{-1}$ (120° C., 60 torr). U.S. Pat. No. 6,538,167 B1 discloses a similar method, suggesting that the reaction conditions shall ensure the alkylation of aromatic compounds.

U.S. Pat. No. 6,710,218 B1 discloses a method for converting methanol into lower olefins, utilizing SAPO-34 as the catalyst. A fluidized bed reactor-regenerator process is used. The selectivity of lower olefins is higher than 90 wt %, in which more than 80 wt % is ethylene and propylene. The ethylene/propylene ratio ranges from 0.69 to 1.36 by the modification of the reaction temperature and space velocity of feed.

U.S. Pat. Nos. 6,437,208 B1 and 6,740,790 B2 disclose a method for making olefins from oxygenate-containing feedstock by employing a fluidized bed reaction technique in the presence of a silicoalumophosphate molecular sieve catalyst. The conversion conditions include that the silicon/aluminum ratio in the catalyst is lower than 0.65; the average catalyst feedstock exposure index (ACFE) is at least 1; and the reaction temperature is 200-700° C., etc.

U.S. Pat. No. 6,455,747 B1 discloses a method for converting oxygenate-containing feed into olefins. The reaction conditions include that the superficial velocity is not lower than 2 m/s and WHSV is 1-5000 hr$^{-1}$. Similar methods are disclosed in U.S. Pat. Nos. 6,552,240 B1 and 6,717,023 B2.

Chinese patent CN1163458C discloses a MTO reaction process using SAPO-34 catalyst and a dense phase fluidized bed. The conversion of methanol is 93-100%. The total selectivity for ethylene and propylene is higher than 80% by weight. The ethylene/propylene ratio of the product may be changed by altering the conditions such as reaction temperature, feeding space velocity and the like.

U.S. Pat. No. 6,613,950 B1 discloses a method for producing olefin from oxygenate-containing feedstock. A silicoalumophosphate molecular sieve is utilized as the catalyst. Following gas stripping, a portion of the exposed catalyst is returned back to the reaction zone without regeneration to be contacted with the feedstock.

U.S. Pat. No. 6,743,747 B1 discloses a method for converting oxygenate feedstock into olefins with a silicoalumophosphate molecular sieve as the catalyst. Aromatic compounds are added to the feed proportionally, so that the yield of olefins, in particular ethylene, is enhanced.

U.S. Pat. No. 6,051,746 A1 discloses a method for converting oxygenate organic material into olefins with small pore molecular sieve catalysts. The catalyst is pre-treated with the aromatic compounds containing nitrogen and at least 3 interconnected rings, in order to decrease the amount of byproducts such as ethane, etc. and increase the yield of olefins.

U.S. Pat. No. 6,518,475 B2 discloses a method for converting oxygenates into lower olefins. The catalyst utilized is a silicoalumophosphate molecular sieve. In order to obtain a higher yield of ethylene, acetone is added to the feed, or the catalyst is pre-treated with acetone.

US patents US20050215840 A1 and U.S. Pat. No. 6,965,057 B2 discloses a method for converting oxygenate feedstock, including methanol, into lower olefins. A riser technique is used. At least a portion of the catalyst deactivated by coking enters the regenerator to burn off the carbonaceous deposit. At least 60% of the molecular oxygen carried by catalyst is then removed by gas stripping. The catalyst is returned back into the reactor to be re-contacted with the feedstock.

U.S. Pat. No. 6,673,978 B2 discloses a method for converting oxygenate feedstock into olefins A silicoalumophosphate molecular sieve is used as the catalyst. The fluidized bed reaction device employed includes at least one reaction zone and one circulation zone. A temperature of 250° C. or higher is set up for the circulation zone, and specified portions of the catalyst circulates between the reaction zone and circulation zone.

Chinese patent CN1356299A discloses a technique utilizing SAPO-34 catalyst and a parallel-flow descending type fluidized bed. With this method, the byproduct such as alkanes, etc. in the MTO procedure is decreased, thus the difficulty of the subsequent separation is lowered. The conversion of methanol is higher than 98%, and the selectivity of olefins is higher than 90 wt %.

Chinese patent CN1190395C discloses a method for producing lower olefins from oxygenate compounds, such as methanol or dimethyl ether, comprising the step of feeding at several locations along the axis direction of the catalyst bed, which improves the selectivity of ethylene.

Chinese patent CN1197835C provides a method for transforming oxygenate compounds into olefins. A main olefin product yield of 45 wt % could be achieved under the conditions that the feeding is carried out while the oxygenate proportion index is at least 0.5; and the partial pressure-rate compensation factor is kept at least $0.1\ psia^{-1}hr^{-1}$.

With the technologies and methods disclosed above, the distributions of products are relatively fixed. Although the composition of products could be modulated by altering the reaction conditions in some of these patented methods, the extent of the modulation is much limited. The changing demand for olefins in the global market, particularly the rapidly increasing demand for propylene in the recent years, requires a more flexible distribution of the olefin products transformed from methanol, especially in the ratio of ethylene to propylene, i.e. the two main olefin products. In view of above, several patents have disclosed the methods for changing the distribution of products by recycling a portion of the products.

U.S. Pat. No. 6,441,262 B1 and Chinese patent CN1489563A disclose methods for transforming oxygenate feedstock into lower olefins, wherein methanol, ethanol, 1-propanol, 1-butanol or mixture thereof is contacted with the catalyst to generate olefins, and then the catalyst is contacted with said oxygenate compounds to generate olefins, so that the ratio of products, including ethylene, propylene and butylene, could be changed without shutdown.

Canadian patent CA2408590 discloses a technique for transforming methanol into propylene. Reactors connected in series are utilized to produce propylene, dimethyl ether and higher hydrocarbon, and the resultant dimethyl ether and a portion of the higher hydrocarbons are returned back into the reactors connected in series and subjected to a further reaction, in order to increase the yield of propylene.

U.S. Pat. Nos. 5,914,438 and 6,303,839 B1 disclose methods for producing lower olefins, including that oxygenate feedstock are contacted with the catalyst containing aluminophosphate and transformed into C2-C4 olefin, and partial C3 and C4 fraction are recycled and cracked to increase the yield of ethylene and propylene. The recycling reaction could be carried out in the riser of the fluidized bed or in a separate reaction zone.

U.S. Pat. No. 5,990,369 disclosed a method for producing lower olefins, including that oxygenate feedstock are contacted with a catalyst containing aluminophosphate and transformed into C2-C4 olefins, and a portion of the olefin products are recycled and cracked to increase the yield of ethylene, propylene and butylenes, wherein either propylene could be recycled to increase production of ethylene, or the ethylene and butylenes could be recycled to increase production of propylene.

The present invention is based on the theory that during the transformation from methanol to olefins, there exist several reaction trends: Certain reaction trends can be enforced by employing different reaction conditions in different reaction zones, so that the composition of the products can be changed. The commonly well known transformation route from methanol to hydrocarbons under acidic catalysts is shown as follows:

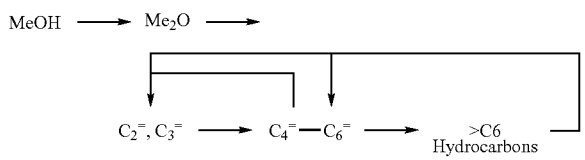

It is a complicated reaction network, roughly including two reaction directions: one is the reactions involving the increase of the number of carbon atoms—light olefins such as ethylene, propylene and the like forms higher hydrocarbon molecules through reactions such as oligomerization and the like; the other one is the reactions involving the reduce of number of carbon atoms—higher hydrocarbon molecules are cracked into light olefin such as ethylene and propylene, etc. In order to obtain lower olefins such as ethylene and propylene, certain reaction conditions such as higher reaction temperature which favors the transformation towards the cracking of higher hydrocarbon are usually required. Another pathway is to utilize the shape selectivity of molecular sieve catalysts to ensure that the reactions occur in the channels so that only the smaller hydrocarbon molecules may diffuse out and lower olefins are formed at a high selectivity. Recently, it has been found in some studies that the reaction types involved in the MTO transformation procedure are more complicated than the above scheme. For instance, Svelle et al has discovered in an isotope research (Kinetic studies of zeolite-catalyzed methylation reactions. *J. Catal.*, 224 (1), 115-123, 2004) that during the transformation from methanol to olefin, alkylation occurs between olefins and methanol, so that the number of carbon atoms in olefin is increased:

$$CH_3OH + C_nH_{2n} = C_{n+1}H_{2n+2} + H_2O$$

In particular, the alkylation between one molecule of ethylene and one molecule of methanol forms one molecule of propylene.

U.S. Pat. No. 3,906,054 discloses a technology for alkylation of olefins, comprising that olefins are contacted with catalysts, i.e. a zeolite with silica to alumina ratio of 12 or higher, in the presence of alkylating agents. P modification is used, wherein the minimum P content is 0.78 wt %. The olefins that may be alkylated include ethylene, propylene, butylene-2 and isobutylene, and the suitable alkylating agents are methanol, dimethyl ether and methyl chloride.

The international patent WO2005/056504 A1 discloses a method for efficiently preparing propylene from ethylene and methanol or/and dimethyl ether, including that ethylene and methanol or/and dimethyl ether react in the presence of catalysts to generate propylene. It is characterized in that the amount of ethylene flowing out of the reaction system is reduced as compared with the amount of ethylene added to the reaction system. The yield of propylene reaches 40 mol % based on the moles of methanol or two times of the moles of dimethyl ether which is added to the reaction system.

DISCLOSURE OF THE INVENTION

The present invention provides a method for converting methanol or/and dimethyl ether into light olefins, whereby the selectivity of lower olefins is improved in the whole process and the ratio of ethylene/propylene of the product is modulated, comprising feeding methanol or/and dimethyl ether at three reaction zones and strengthening the following two reaction trends, wherein one is to strengthen the cracking of higher olefins to increase the total yield of ethylene and propylene; and the other is to strengthen the alkylation of ethylene and methanol or/and dimethyl ether to co-transform a portion of ethylene and methanol or/and dimethyl ether into propylene.

The present invention provides a method for transforming methanol or/and dimethyl ether into light olefins, characterized in that at least 3 independent reaction zones and at least one separation zone are employed. The feedstock of methanol or/and dimethyl ether is divided into 3 streams. The first stream enters the first reaction zone, being contacted with a molecular sieve catalyst and transformed into a mixture of ethylene, propylene, butylenes and higher hydrocarbons. The catalyst used in such reaction zone can be a silica-alumina zeolite or/and a silicophosphate molecular sieve, with a pore size of 0.3-0.6 nm, such as ZSM-5, ZSM-11, SAPO-34, SAPO-11, etc., and their derivatives obtained by elemental modification. The contact of the feedstock (i.e. methanol or/and dimethyl ether) with the catalyst is performed in reactors such as fixed beds, fluidized beds or risers, etc. In the case of fixed bed reactors, a series of reactors in this reaction zone are set for alternative switches to regeneration state. In the case of fluidized bed and riser reactors, the devices for continuous catalyst regeneration are included. The reaction conditions should ensure a conversion of methanol or/and dimethyl ether higher than 99%, a sufficiently high yield of ethylene and propylene, and an as low as possible yield of low-value products such as methane and coke. The suitable reaction temperature in said reaction zone is 350-700° C.

The stream flowing out of the reaction zone described above enters into said separation zone to undergo a preliminary separation. The streams flowing out of the other two reaction zones enter into said separation zone as well. Three effluent streams are formed from said separation zone, including a stream containing ethylene, ethane, and lighter fractions; a stream containing propylene and propane; and a stream containing C4 and heavier fractions. Among them, the stream containing propylene and propane fractions undergoes a further separation to remove propane and form a propylene product. At least a portion of the stream containing ethylene, ethane and lighter products enters the second reaction zone, and the rest are led to a further separation to remove other fractions to form ethylene product. At least a portion of the stream containing C4 and heavier fractions enters the third reaction zone, and the rest part forms a mixed hydrocarbon product with carbon atoms of 4 and more, or forms C4 product, C5 product and the like by further separation.

The second stream of methanol or/and dimethyl ether enters the second reaction zone. At the same time, at least a portion of said stream containing ethylene, ethane and lighter products which comprise $C_2H_4$, $C_2H_6$, $CH_4$, $H_2$ and $CO_x$ (x=1 or 2), etc., coming from the separation zone, enters into the same reaction zone. After sufficiently mixed, these two streams are contacted with a molecular sieve catalyst, so that a mixed stream containing propylene are generated and in turn fed into the separation zone. The catalysts used in this reaction zone can be a silica-alumina zeolite, a silicophosphate molecular sieve, with a pore size of 0.3-0.6 nm, such as ZSM-5, ZSM-11, SAPO-34, SAPO-11, etc., or their derivatives obtained by elemental modification. The reaction conditions should ensure that the conversion of methanol or/and dimethyl ether is greater than 99% and that the propylene is generated at high selectivity. The suitable reaction temperature in such reaction zone is 250-600° C. The contact between the feedstock mixture and the catalyst can be performed in various kinds of reactors including fixed beds, fluidized beds and risers, etc. In the case of fixed bed reactors, a series of reactors are included in this reaction zone for alternative switches to regeneration state. In the case of fluidized bed and riser reactors, the devices for continuous regeneration catalysts are included.

The third stream of methanol or/and dimethyl ether enters the third reaction zone. At the same time, at least a portion of the stream containing C4 and heavier fractions, coming from the separation zone, enters into the same reaction zone. This stream containing C4 and heavier fractions are contacted with a catalyst in the third reaction zone and cracked to form a mixed product comprising ethylene and propylene. The cracking reaction is endothermic, and the reaction heat is at least partially provided by the transformation of the feedstock of methanol or/and dimethyl ether which is introduced into said reaction zone, in the presence of a catalyst. Methanol or/and dimethyl ether contacts the catalyst either together with said stream containing C4 and heavier fractions, or at different sections in the same reaction zone and indirectly provide the heat for the cracking reaction of the latter. Meanwhile, the contacting of methanol or/and dimethyl ether with the catalyst generates products including ethylene, propylene and C4 and heavier fractions. The catalysts used in such reaction zone can be a silica-alumina zeolite or a silicophosphate molecular sieve, with a pore size of 0.3-0.6 nm, such as ZSM-5, ZSM-11, SAPO-34, SAPO-11, etc., and/or their derivatives obtained by element modification. The reaction conditions should ensure that the conversion of methanol or/and dimethyl ether is greater than 99% and that the ethylene and propylene are generated at high selectivity. The suitable reaction temperature in said reaction zone is 450-700° C. The contact between the material streams and the catalyst can be done in all kinds of reactors including fixed beds, fluidized beds and risers, etc. The stream flowing out of the reactor contains ethylene, propylene and C4 and heavier fractions and enters into the separation zone described above.

In the above method, a portion of the stream containing ethylene, ethane and lighter products, coming from said separation zone, enters the second reaction zone, and a portion of the stream containing C4 and heavier fractions, coming from said separation zone, enters the third reaction zone, at certain proportions, respectively. These two proportions change from 1% to 99% by weight. The stream of methanol or/and dimethyl ether that enters into the second reaction zone accounts for 1-30% of the total stream of methanol or/and dimethyl ether by weight. The stream of methanol or/and dimethyl ether that enters into the third reaction zone accounts for 1-40% of the total stream of methanol or/and dimethyl ether by weight. In the distribution of the final olefin products, the ethylene/propylene ratio is 0-2.0 (by weight).

Based on the above disclosure of the invention, the present invention can be summarized as follow:

The present invention provides a method for converting methanol or/and dimethyl ether into light olefins, characterized in that at least three independent reaction zones and at least one separation zone are employed, and that all feedstock of methanol or/and dimethyl ether are divided into three parts and fed at said independent reaction zones, and that the ratio of different types of olefins in the final product can be modulated by changing the feeding ratio for each reaction zone, the method comprising the steps of: (a) converting methanol or/and dimethyl ether into a mixed hydrocarbon stream that contains ethylene, propylene and olefin with 4 and more carbon atoms in the presence of acidic catalysts in the first reaction zone, and leading said hydrocarbon stream into said separation zone; (b) carrying out the separation of all the effluent streams of said three reaction zones in said separation zone to form a C3 fraction which flows out of said separation zone to form a propylene product by further separation, a fraction with no more than 2 carbon atoms and a fraction with 4 or more carbon atoms, at least a portion of said effluent stream with no more than 2 carbon atoms being led into the second reaction zone with the rest being further separated to obtain ethylene product, at least a portion of said effluent stream with 4 or more carbon atoms being led into the third reaction zone with the rest being further separated to obtain butylene product; (c) contacting the methanol or/and dimethyl ether together with at least a portion of effluent stream coming from said separation zone and containing no more than 2 carbon atoms with an acidic catalyst in the second reaction zone and leading the formed mixture containing propylene into said separation zone; (d) contacting methanol or/and dimethyl ether as well as at least a portion of said effluent stream coming from said separation zone and containing 4 or more carbon atoms with an acidic catalyst in the third reaction zone, and leading the resultant mixture containing certain concentration of ethylene and propylene into said separation zone.

According to the above method, the stream of methanol or/and dimethyl ether that enter(s) the second reaction zone accounts for 1-30 wt % of the total stream of methanol or/and dimethyl ether. The stream of methanol or/and dimethyl ether that enter(s) the third reaction zone accounts for 1-40 wt % of the total stream of methanol or/and dimethyl ether. 1-99 wt % of the stream flowing out of the separation zone and containing 2 or fewer carbon atoms enters the second reaction zone. 1-99 wt % of the stream flowing out of the separation zone and containing 4 or fewer carbon atoms enters the third reaction zone.

According to the above method, the catalysts used in each reaction zone may include a silica-alumina zeolite or/and a silicophosphate molecular sieve, and their derivatives obtained by elemental modification. The pore sizes for the silica-alumina zeolite or/and silicophosphate molecular sieve are 0.3-0.6 nm. The catalysts include matrix materials comprising one or more of silica, alumina or clay.

According to the method of the present invention, the reaction temperature in the first reaction zone is 350-700° C.; the reaction temperature in the second reaction zone is 250-600° C.; and the reaction temperature in the third reaction zone is 450-700° C.

According to the method of the present invention, fluidized beds, fixed beds or moving bed reactors can be utilized in the first, second and third reaction zone, respectively.

BRIEF DESCRIPTION OF THE DRAWING

FIG. 1 is the schematic flow chart of the method according to the present invention. As shown in FIG. 1, all the feedstock of methanol or/and dimethyl ether is divided into 3 streams. The stream 8 of methanol of/and dimethyl ether enters into the reaction zone 1, and is transformed into a mixed stream 11 containing ethylene, propylene, butylenes and hydrocarbon with more carbon atoms. The mixed stream 11 then enters into the separation zone 4 and undergoes a preliminary separation. The stream 12 flowing out of the reaction zone 2 and the stream 13 flowing out of the reaction zone 3 enter into the separation zone 4 as well. Three effluent streams are formed from the separation zone 4, including the stream containing ethylene, ethane and lighter fractions; the stream containing propylene and propane; and the stream containing C4 and heavier fractions. Among them, the stream 16 containing propylene and propane undergoes a separation step in the separation zone 5, so that propane is removed and the propylene product 19 is generated. At least a portion of the stream containing ethylene, ethane and lighter products (stream 14) enters into the reaction zone 2, with the rest (stream 17) entering into the separation zone 6 and going through a separation step to remove fractions other than ethylene to form the ethylene product 20. At least a portion of the stream containing C4 and heavier fractions (stream 15) enters into the reaction zone 3, with the rest forming a mixed hydrocarbon product with 4 or more carbon atoms (stream 18) or undergoing a separation step in the separation zone 7 to form products as C4 product (stream 21) and products with 5 or more carbon atoms. The stream 9 of methanol or/and dimethyl ether enters into the reaction zone 2. At the same time, the stream 14 flowing out of the separation zone 4 and containing ethylene, ethane and lighter products enters into the same reaction zone, and the stream 12 flowing out of the reaction zone 2 and containing propylene enters into the separation zone 4. The stream 10 of methanol or/and dimethyl ether enters into the reaction zone 3. At the same time, a portion of stream flowing out of separation zone 4 and containing C4 and heavier fractions (stream 15) enters into the same reaction zone, and the stream 13 flowing out of the reaction zone 3 and containing ethylene, propylene and hydrocarbons with 4 and more carbon atoms enters into the separation zone 4.

EMBODIMENTS OF THE INVENTION

The present invention will now be further illustrated in details by the following Examples, which shall not be construed to be a limitation for the scope of invention in any way.

EXAMPLE 1

The Conversion of Methanol Over a Molecular Sieve Catalyst

Catalyst A was prepared as follows: after mixed with silicasol (Zhejiang Yuda Chemical Industry CO., Ltd.) completely, a ZSM-5 molecular sieve (The Catalyst Plant of Nankai University, with silicon/aluminum ratio of 50) was shaped by mixing, kneading and extruding; air dried at room temperature; and further baked at 550° C. for 4 hours. The above samples were immersed in a lanthanum nitrate solution of a certain concentration, and baked to dryness. Then, the resultant material was immersed in a phosphoric acid solution of a certain concentration, and baked to dryness (lanthanum nitrate, analytical pure, Tianjin Kermel Chemical Reagent Co., Ltd., phosphoric acid, 85%, The Chemical Reagent factory of Shenyang). The resulting material was catalyst A. The contents of ZSM-5, P and La in the catalyst were 85 wt %, 2.10 wt % and 1.05 wt %, respectively.

The reactions were carried out in a micro fixed bed reaction device under the following reaction conditions: the charge of catalyst A was 3 g; the reaction temperature was 550° C.; the feedstock was an 80 wt % aqueous methanol; the weight hourly space velocity (WHSV) of methanol was 1.5 hr$^{-1}$; and the reaction pressure was 0.1 MPa. The resulting product was analyzed by a Varian CP-3800 Gas Chromatograph (Plot Capillary Column, programmed heating from 50° C. to 200° C., FID).

The results of the reaction were shown in Table 1. As shown, the selectivities of ethylene, propylene and butylenes were about 23-26 wt %, 33-35 wt % and 19-20 wt %, respectively. The ethylene/propylene ratio was 0.6-0.8 (weight ratio).

TABLE 1

Results of Reactions in Example 1

| | Reaction Time (min.) | |
|---|---|---|
| | 60 | 180 |
| Selectivity (wt %) | | |
| $C_2H_4$ | 23.08 | 25.83 |
| $C_3H_6$ | 34.80 | 33.82 |
| $C_4H_8$ | 19.33 | 19.34 |
| $CH_4$ | 1.70 | 1.58 |
| $C_2H_6 + C_3H_8 + C_4H_{10}$ | 3.66 | 5.33 |
| $C_5+$ | 6.90 | 4.92 |
| $CO_X (X = 1, 2)$ | 3.91 | 2.69 |
| $C_2H_4/C_3H_6$ | 0.66 | 0.76 |
| Conversion of Methanol(wt %) | 100 | 100 |

EXAMPLE 2

The Conversion of Methanol Over a Molecular Sieve Catalyst

Catalyst B was prepared as follows: SAPO-34 (provided by Dalian Institute of Chemical Physics) was mixed well with clay, aluminum sol and silicasol (all commercially available from Zhejiang Yuda Chemical Industry CO., Ltd.), and dispersed in water to form a slurry. After shaping by spraying, microspheres with diameter of 20-100 μm were formed. The microspheres were baked at 600° C. for 4 hours, and the resultant was catalyst B. The content of SAPO-34 in the catalyst was 30 wt %.

TABLE 2

Results of Reactions in Example 2

| | Reaction Temperature (° C.) | |
|---|---|---|
| | 450 | 500 |
| | Catalysts Recycle (g/hr) | |
| | 465 | 900 |
| Selectivity of Hydrocarbon (wt %) | | |
| $C_2H_4$ | 42.58 | 48.50 |
| $C_3H_6$ | 38.63 | 32.12 |
| $CH_4$ | 1.12 | 2.39 |
| $C_2H_6 + C_3H_8$ | 3.25 | 3.94 |
| $C_4$ | 10.96 | 9.75 |
| $C_5+$ | 3.47 | 3.21 |
| $C_2H_4/C_3H_6$ | 1.10 | 1.51 |
| Conversion of Methanol (wt %) | 99.13 | 100 |

The reactions were carried out in a pilot fluidized bed reaction device under the reaction conditions as follows: the total charge of catalyst B was 5 Kg and the charge for the reactor bed was 1.25 Kg; the recycle rate of the catalyst was 0.4-1 Kg/hr; the reaction temperature was 450-500° C.; the feed was an 80 wt % aqueous methanol solution; the WHSV was 1.8 hr$^{-1}$, and the reaction pressure was 0.1 MPa. The reaction product was analyzed by a Varian CP-3800 Gas Chromatography with a Plot Column and a FID.

The results of the reactions were shown in Table 2. As shown, the selectivities of ethylene and propylene were about 42-49 wt % and 32-39 wt %, respectively. The total selectivity of ethylene and propylene was 80-82 wt %. The ratio of ethylene/propylene was 1.0-1.5 by weight.

EXAMPLE 3

The Reactions of Co-Feeding of Ethylene and Methanol Over a Molecular Sieve Catalyst Catalyst C was prepared as follows: after mixed with silicasol homogeneously, SAPO-34 (the raw materials and their sources are same as those in Examples 1 and 2) was shaped by mixing, kneading and extruding; air dried at room temperature; and baked at 550° C. for 4 hours. The resultant was catalyst C.

The reactions were carried out in a micro fixed bed reaction device under the following reaction conditions: the charge of catalyst C was 1 g; the reaction temperature was 450° C.; the feedstock was a mixture of methanol and ethylene with the methanol content (C mol %) of 6-30%; the reaction contacting time was 1 s; and the reaction pressure was 0.1 MPa. The resulting product was analyzed by a Varian CP-3800 Gas Chromatography with a Plot Column and a FID. The sampling time was 6 min.

The results of the reactions were shown in Table 3. As shown, the yield of $C_3H_6$ calculated on the basis of MeOH reached 90 wt % or higher.

TABLE 3

Results of Reactions in Example 3

| Composition of Reaction Inlet/ C Mol % | | | |
|---|---|---|---|
| $C_2H_4$ | 93.33 | 87.50 | 71.43 |
| MeOH | 6.67 | 12.50 | 28.57 |
| Composition of Reaction Outlet/C Mol % | | | |
| $C_2H_4$ | 89.28 | 85.33 | 77.66 |
| $C_3H_6$ | 6.26 | 8.68 | 13.13 |
| $C_4+$ | 3.46 | 4.64 | 7.31 |
| Others | 1.00 | 1.35 | 1.90 |
| Conversion of MeOH (%) | 100 | 99.57 | 99.96 |
| Yield of $C_3H_6$ based on MeOH (wt %) | 93.79 | 69.78 | 45.96 |

EXAMPLE 4

The Reactions of the Co-Feeding of Ethylene-Containing Gas Mixture and Methanol Over a Molecular Sieve Catalyst Catalyst D was prepared as follows: after immersing in a magnesium nitrate solution and being dried off, a ZSM-5 molecular sieve was baked at 550° C. The resulting sample was mixed with clay, aluminum sol and silicasol, and dispersed in water to form a slurry. After shaping by spraying, microspheres with a diameter of 20-100 μm were formed (the raw materials and their sources are same as those in Examples 1 and 2). The microspheres were baked at 550° C. for 4 hours, and the resultant was catalyst D. The contents of ZSM-5 and Mg in the catalyst were 30 wt % and 0.5 wt %, respectively.

The reactions were carried out in a micro fluidized bed reaction device. The charge of the catalyst was 10 g; the reaction temperature was 425° C.; the liquid feedstock was an aqueous 30 wt % methanol solution; and the WHSV of methanol was 2.0 $hr^{-1}$. The gaseous feedstock was ethylene-containing gas mixture with the detailed composition shown in Table 4. The feeding ratio of ethylene/methanol was 3.5, and the reaction pressure was 0.1 MPa. The resulting product was analyzed by a Varian CP-3800 Gas Chromatography with a Plot Column and a FID.

The results of the reactions were shown in Table 5. As shown, conversion of methanol was 95-97%, and the yield of propylene calculated on the basis of methanol was 83 wt %.

TABLE 4

Composition Analysis of Ethylene-Containing Gas Mixture

| | Composition | | | | | | |
|---|---|---|---|---|---|---|---|
| Ethylene | Methane | Ethane | C4= | C5= | CO | $CO_2$ | $H_2$ |
| Mol % 71.6 | 7.73 | 0.03 | 0.006 | 0.004 | 7.6 | 2.88 | 10.2 |

TABLE 5

Results of Reactions in Example 4

| | Time On Line/min. | |
|---|---|---|
| | 6 | 34 |
| Hydrocarbon Composition of Outlet/C Mol % | | |
| $C_2H_4$ | 73.48 | 72.48 |
| $C_3H_6$ | 9.86 | 9.90 |
| $C_4H_8$ | 4.74 | 5.24 |
| Conversion of Methanol/% | 95.3 | 97.0 |
| Yield of Propylene based on Moles of Methanol (wt %) | 82.9 | 83.3 |

EXAMPLE 5

The Reactions of the Co-Feeding of Butylene and Methanol Over a Molecular Sieve Catalyst The catalyst used was same as that in Example 2. The reactions were carried out in a micro fixed bed reaction device under the following reaction conditions: the charge of catalyst C was 1 g; the reaction temperature was 450° C.; the feed was a mixture of methanol and butylenes-2 with the butylenes/methanol ratio of 5.24 (weight ratio); the WHSV based on methanol was 2.0 $hr^{-1}$, and the reaction pressure was 0.1 MPa. The reaction product was analyzed by a Varian CP-3800 Gas Chromatography with a Plot Column and a FID.

TABLE 6

Results of Reactions in Example 5

| Compositions of Reaction Inlet/ C Mol % | |
|---|---|
| $C_4H_8$ | 92.45 |
| MeOH | 7.55 |
| Compositions of Reaction Outlet/C Mol % | |
| $C_2H_4$ | 5.76 |
| $C_3H_6$ | 20.72 |
| $C_4$+ | 71.70 |
| Others | 1.81 |
| Conversion of MeOH (%) | 100 |
| Conversion of $C_4H_8$ (%) | 30.83 |

EXAMPLE 6

The reaction flow in FIG. 1 was utilized. Fluidized bed reactors were used in each reaction zone, and the reaction conditions such as catalysts, reaction temperature, pressure and WHSV, etc. were shown in Table 7.

TABLE 7

Reaction Conditions of Each Reaction Zone in Example 6

| Reaction Zone | Temperature (° C.) | Pressure (MPa, Gauge Pressure) | WHSV ($hr^{-1}$) | Catalysts |
|---|---|---|---|---|
| 1 | 450 | 0.2 | 2.0 | Catalyst B |
| 2 | 450 | 0.2 | 1.5 | Catalyst D |
| 3 | 475 | 0.2 | 2.0 | Catalyst B |

TABLE 8

Composition of Each Stream in Example 6

| Stream No. | Flow Rate (ton/hr) | Detailed Composition (ton/hr) | |
|---|---|---|---|
| 8 | 228 | methanol | |
| 9 | 47 | methanol | |
| 10 | 13 | methanol | |
| 11 | 98 | hydrogen, carbon oxides, methane, ethane | 3 |
| | | ethylene | 39 |
| | | propylene | 39 |
| | | propane | 2 |
| | | hydrocarbons with 4 or more carbon atoms | 15 |
| 12 | 138.3 | hydrogen, carbon oxides, methane, ethane | 18.2 |
| | | ethylene | 80 |
| | | propylene | 30 |
| | | propane | 0.1 |
| | | hydrocarbons with 4 or more carbon atoms | 10 |
| 13 | 71.5 | hydrogen, carbon oxides, methane, ethane | 1 |
| | | ethylene | 4.3 |
| | | propylene | 14.8 |
| | | propane | 0.2 |
| | | hydrocarbons with 4 or more carbon atoms | 51.2 |
| 14 | 118 | hydrogen, carbon oxides, methane, ethane | 18 |
| | | ethylene | 100 |
| 15 | 66 | hydrocarbon with 4 or more carbon atoms | |
| 16 | 86.1 | propylene | 83.8 |
| | | propane | 2.3 |
| 17 | 27.5 | hydrogen, carbon oxides, methane, ethane | 4.2 |
| | | ethylene | 23.3 |
| 18 | 10.2 | hydrocarbons with 4 or more carbon atoms | |

The total feeding amount of methanol was 288 ton/hr, and the methanol feed was divided into 3 streams, i.e. stream 8, stream 9 and stream 10, with the proportions of 79.2 wt %, 16.3 wt % and 4.5 wt %, respectively. Methanol stream 8 (the flow rate of methanol was 228 ton/hr) entered into the reaction zone 1 and was transformed into the mixed stream 11 (with a flow rate of 98 ton/hr), including ethylene, propylene, butylenes and hydrocarbons with more carbon atoms. The stream 11 then entered into the separation zone 4 to undergo a preliminary separation. The streams 12 and 13 flowing out of the reaction zone 2 and 3, respectively, entered into the separation zone 4 as well. Three effluent streams, i.e., the materials containing ethylene, ethane and lighter fractions; the materials containing propylene and propane; and the materials containing C4 and heavier fractions, respectively, were formed in the separation zone 4. Among them, the stream 16 (with a flow rate of 86.1 ton/hr) containing propylene and propane underwent a separation step in the separation zone 5, so that propane was removed and the propylene product was generated. A portion of the material containing ethylene, ethane and lighter products (stream 14, with a flow rate of 118 ton/hr) entered the reaction zone 2, with the rest (stream 17, with a flow rate of 27.5 ton/hr) entering the separation zone 6 to remove fractions other than ethylene. At least a portion of the material containing C4 and heavier fractions (stream 15, with a flow rate of 66 ton/hr) entered into the reaction zone 3, with the rest part (stream 18, 10.2 ton/hr) forming hydrocarbon products with 4 or more carbon atoms, or entering the separation zone 7 to form C4 product and product with 5 or more carbon atoms. The stream 12 (with a flow rate of 138.3 ton/hr) flowing out of the reaction zone 2 and containing propylene, and the stream 13 (with a flow rate of 71.5 ton/hr) flowing out of the reaction zone 3 and containing ethylene, propylene and hydrocarbons with 4 and more carbon atoms, entered into the separation zone 4.

The flow rates and compositions of each stream in the flow chart were shown in details in Table 8. Calculated on the basis of total flow rate of the methanol feed and the composition of stream 16, 17 and 18, the selectivity of propylene obtained by the technical process described above was 66.5 wt %. The total selectivity of ethylene and propylene was 85 wt %. The ratio of ethylene/propylene was 0.28 (weight ratio).

EXAMPLE 7

The reaction flow, the type of reactors and catalysts in each reaction zone were as same as those in Example 6. The reaction conditions, such as temperature, pressure and WHSV, etc. were shown in Table 9.

TABLE 9

Reaction Conditions of Each Reaction Zone in Example 7

| Reaction Zone | Temperature (° C.) | Pressure (MPa, Gauge Pressure) | WHSV (hr$^{-1}$) | Catalysts |
|---|---|---|---|---|
| 1 | 450 | 0.2 | 2.0 | Catalyst B |
| 2 | 450 | 0.3 | 2.3 | Catalyst D |
| 3 | 475 | 0.3 | 3.0 | Catalyst B |

TABLE 10

Composition of Each Stream in Example 7

| Stream No. | Flow Rate (ton/hr) | Detailed Composition (ton/hr) | |
|---|---|---|---|
| 8 | 228 | Methanol | |
| 9 | 70.5 | Methanol | |
| 10 | 19.5 | Methanol | |
| 11 | 98 | hydrogen, carbon oxides, methane, ethane | 3 |
|   |    | ethylene | 39 |
|   |    | propylene | 39 |
|   |    | propane | 2 |
|   |    | hydrocarbons with 4 or more carbon atoms | 15 |
| 12 | 225.9 | hydrogen, carbon oxides, methane, ethane | 45.7 |
|   |    | ethylene | 120 |
|   |    | propylene | 45 |
|   |    | propane | 0.2 |

TABLE 10-continued

Composition of Each Stream in Example 7

| Stream No. | Flow Rate (ton/hr) | Detailed Composition (ton/hr) | |
|---|---|---|---|
|   |    | hydrocarbons with 4 or more carbon atoms | 15 |
| 13 | 107.3 | hydrogen, carbon oxides, methane, ethane | 1.5 |
|   |    | ethylene | 6.5 |
|   |    | propylene | 22.2 |
|   |    | propane | 0.3 |
|   |    | hydrocarbons with 4 or more carbon atoms | 76.8 |
| 14 | 195.5 | hydrogen, carbon oxides, methane, ethane | 45.5 |
|   |    | ethylene | 150 |
| 15 | 99 | hydrocarbons with 4 or more carbon atoms | |
| 16 | 108.7 | propylene | 106.2 |
|   |    | propane | 2.5 |
| 17 | 20.2 | hydrogen, carbon oxides, methane, ethane | 4.7 |
|   |    | ethylene | 15.5 |
| 18 | 7.8 | hydrocarbons with 4 or more carbon atoms | |

The total feeding flow rate of methanol was 318 ton/hr, and the methanol feedstock was divided into 3 streams, i.e. stream 8, stream 9 and stream 10, with the proportions of 71.7 wt %, 22.2 wt % and 6.1 wt %, respectively. The flow rate and composition of each stream in the flow chart were shown in details in Table 10. Calculated on the basis of the total flow rate of the feedstock, i.e. methanol, and the composition of stream 16, 17 and 18, the selectivity of propylene obtained by the technical process described above was 76.4 wt %. The total selectivity of ethylene and propylene was 87.6 wt %. The ratio of ethylene/propylene was 0.15 (weight ratio).

EXAMPLE 8

The reaction flow, the type of reactors and catalysts in each reaction zone were as same as those in Example 8. The reaction conditions, such as temperature, pressure and WHVS, etc. were shown in Table 11.

TABLE 11

Reaction Conditions of Each Reaction Zone in Example 7

| Reaction Zone | Temperature (° C.) | Pressure (MPa, Gauge Pressure) | WHSV (hr$^{-1}$) | Catalysts |
|---|---|---|---|---|
| 1 | 450 | 0.2 | 2.0 | Catalyst B |
| 2 | 450 | 0.3 | 2.3 | Catalyst D |
| 3 | 475 | 0.3 | 3.0 | Catalyst B |

TABLE 12

Composition of Each Stream in Example 8

| Stream No. | Flow Rate (ton/hr) | Detailed Composition (ton/hr) | |
|---|---|---|---|
| 8 | 163.9 | dimethyl ether | |
| 9 | 50.7 | dimethyl ether | |
| 10 | 14 | dimethyl ether | |
| 11 | 98 | hydrogen, carbon oxides, methane, ethane | 3 |
|   |    | ethylene | 39 |
|   |    | propylene | 39 |
|   |    | propane | 2 |
|   |    | hydrocarbon with 4 or more carbon atoms | 15 |
| 12 | 225.9 | hydrogen, carbon oxides, methane, ethane | 45.7 |
|   |    | ethylene | 120 |
|   |    | propylene | 45 |
|   |    | propane | 0.2 |
|   |    | hydrocarbon with 4 or more carbon atoms | 15 |

TABLE 12-continued

Composition of Each Stream in Example 8

| Stream No. | Flow Rate (ton/hr) | Detailed Composition (ton/hr) | |
|---|---|---|---|
| 13 | 107.3 | hydrogen, carbon oxides, methane, ethane | 1.5 |
|  |  | ethylene | 6.5 |
|  |  | propylene | 22.2 |
|  |  | propane | 0.3 |
|  |  | hydrocarbon with 4 or more carbon atoms | 76.8 |
| 14 | 195.5 | hydrogen, carbon oxides, methane, ethane | 45.5 |
|  |  | ethylene | 150 |
| 15 | 99 | hydrocarbon with 4 or more carbon atoms |  |
| 16 | 108.7 | propylene | 106.2 |
|  |  | propane | 2.5 |
| 17 | 20.2 | Hydrogen, carbon oxides, methane, ethane | 4.7 |
|  |  | ethylene | 15.5 |
| 18 | 7.8 | hydrocarbon with 4 or more carbon atoms |  |

The total feeding flow rate of dimethyl ether was 228.6 ton/hr, and the dimethyl ether feedstock was divided into 3 streams, i.e. stream 8, stream 9 and stream 10, with the proportions of 71.7 wt %, 22.2 wt % and 6.1 wt %, respectively. The flow rate and composition of each stream in the flow chart were shown in details in Table 12. calculated on the basis of total flow of the feedstock, i.e. dimethyl ether, and the composition of stream 16, 17 and 18, the selectivity of propylene obtained by the technical method described above was 76.4 wt %. The total selectivity of ethylene and propylene was 87.6 wt %. The ratio of ethylene/propylene was 0.15 (weight ratio).

What is claimed is:

1. A method for converting methanol or/and dimethyl ether into light olefins, characterized in that at least three independent reaction zones and at least one separation zone are employed, wherein all feedstock of methanol or/and dimethyl ether is divided to be fed at said three independent reaction zones, and the distribution of the olefins in the final product can be adjusted by changing the feeding proportion for each reaction zone, the method comprising the steps of:
   (a) transforming methanol or/and dimethyl ether into a mixed stream of hydrocarbons that contains ethylene, propylene and olefins with 4 and more carbon atoms in the presence of acidic catalyst(s) in the first reaction zone, and feeding said stream directly into said separation zone;
   (b) separating the streams flowing out of said three reaction zones in said separation zone, the effluent of C3 fractions flowing out of said separation zone and forming a propylene product upon a further separation, at least a portion of the effluent of fractions with no more than 2 carbon atoms entering into the second reaction zone and the rest being further separated to obtain an ethylene product, and at least a portion of the effluent of fractions with 4 or more carbon atoms entering into the third reaction zone and the rest being further separated to obtain a butylene product;
   (c) contacting the methanol or/and dimethyl ether together with at least a portion of the fractions that come from said separation zone and contain no more than 2 carbon atoms with acidic catalyst(s) in the second reaction zone, and feeding the resultant mixed materials containing propylene directly into said separation zone; and
   (d) contacting methanol or/and dimethyl ether together with at least a portion of the fractions that come from said separation zone and contain 4 or more carbon atoms with acidic catalyst(s) in the third reaction zone, and feeding the resultant mixed materials containing ethylene and propylene directly into said separation zone.

2. The method according to claim 1, wherein the flow rate of methanol or/and dimethyl ether flowing into the second reaction zone accounts for 1-30 wt % of the total flow rate of methanol or/and dimethyl ether.

3. The method according to claim 1, wherein the flow rate of methanol or/and dimethyl ether flowing into the third reaction zone accounts for 1-40 wt % of the total flow rate of methanol or/and dimethyl ether.

4. The method according to claim 1, wherein 1-99 wt % of the materials flowing out of the separation zone and containing no more than 2 carbon atoms enter into the second reaction zone.

5. The method according to claim 1, wherein 1-99 wt % of the materials flowing out of the separation zone and containing 4 or more carbon atoms enter into the third reaction zone.

6. The method according to claim 1, wherein the catalyst(s) used in each reaction zone contain silica-alumina zeolite(s) or/and a silicophosphate molecular sieve(s), and their derivatives obtained by elemental modification.

7. The method according to claim 6, wherein the pore size of said silica-alumina zeolite or said silicophosphate molecular sieve is 0.3-0.6 nm.

8. The method according to claim 6, wherein said catalyst(s) contain matrix materials comprising one or more of silicon oxide, aluminum oxide or clay.

9. The method according to claim 1, wherein the reaction temperature in the first reaction zone is 350-700° C.

10. The method according to claim 1, wherein the reaction temperature in the second reaction zone is 250-600° C.

11. The method according to claim 1, wherein the reaction temperature in the third reaction zone is 450-700° C.

12. The method according to claim 1, wherein fluidized bed(s), fixed bed(s) or moving bed reactor(s) are utilized in the first, second and third reaction zone, respectively.

* * * * *